US005788064A

United States Patent [19]

Sacherer et al.

[11] Patent Number: 5,788,064

[45] Date of Patent: Aug. 4, 1998

[54] STORAGE CONTAINER FOR TEST STRIPS

[75] Inventors: Klaus-Dieter Sacherer, Kirchheim; Gregor Bainczyk, Mannheim, both of Germany

[73] Assignee: Boehringer Mannheim GmbH, Mannheim, Germany

[21] Appl. No.: 766,694

[22] Filed: Dec. 13, 1996

[30] Foreign Application Priority Data

Dec. 14, 1995 [DE] Germany ........................ 195 46 684.5

[51] Int. Cl.[6] .................................................... B65D 43/26

[52] U.S. Cl. .......................... 206/204; 206/449; 220/281; 220/339; 220/344

[58] Field of Search .................................... 206/204, 449, 206/494, 569, 807; 220/281, 260, 324, 335, 339, 344

[56] References Cited

U.S. PATENT DOCUMENTS

| | | | |
|---|---|---|---|
| 3,701,452 | 10/1972 | Tonn | 220/46 R |
| 3,907,103 | 9/1975 | Shaw | 206/540 |
| 3,968,880 | 7/1976 | Ostrowsky | 206/540 |
| 4,042,105 | 8/1977 | Taylor | 206/807 |
| 4,711,360 | 12/1987 | Ullman | 220/335 |
| 4,717,018 | 1/1988 | Sacherer et al. | |
| 4,834,234 | 5/1989 | Sacherer et al. | |
| 5,205,431 | 4/1993 | Zinnbauer | 220/326 |
| 5,505,308 | 4/1996 | Eikmeier et al. | |
| 5,620,107 | 4/1997 | Takeuchi | 220/335 |
| 5,699,912 | 12/1997 | Ishikawa et al. | 206/494 |

FOREIGN PATENT DOCUMENTS

| | | |
|---|---|---|
| 0 538 067 A1 | 10/1992 | European Pat. Off. . |
| 3411920 | 10/1984 | Germany . |
| 43 28 815 | 3/1995 | Germany . |

*Primary Examiner*—Jimmy G. Foster
*Attorney, Agent, or Firm*—Nikaido, Marmelstein, Murray & Oram LLP

[57] ABSTRACT

Storage container for test strips with a holder in which the test strips are contained and which is closed by a lid. The lid has an elastic seal on its inner side which, when the storage container is closed presses against a rim of the holder preventing an invasion of moisture into the storage container. Holder and lid are connected to one another by a hinge. When the storage container is closed, the seal is deformed and pushes the lid after release of a locking means such that the storage container is at least partially opened.

30 Claims, 6 Drawing Sheets

Y

X 3
6
3
3
4
1
2

5
3
4
1
2

4
15
16
6

3
22
21
2
20
5

4
30
20
3
23
23
5
3
4
30
31
2

STORAGE CONTAINER FOR TEST STRIPS

The invention concerns a storage container for test strips with a holder having an orifice which is bordered by a rim, a lid which is connected to the holder by a hinge and which has an elastic seal on its inner side, which tightly urges against the rim of the holder when the storage container is closed, and a releasable locking means, which holds the storage container closed, whereby the elastic seal is deformed when the storage container is closed but returns to its non-deformed shape (rest geometry) when the locking means is released, whereby the lid is flipped around an axis of the hinge thereby leaving the storage container at least partly open.

In the prior art numerous containers for the storage of test strips are known. Despite its rather poor handling characteristics, a storage container in the form of a cylinder with a sealing stopper having a desiccant on its inner side is frequently employed. Whilst this packaging form ensures that the test strips are very effectively protected against moisture, mechanical force and soiling, it has the disadvantage that the stopper is difficult to remove when it is designed to create a sufficient seal. Further more the removal of test strips from the opened tube is a process which poses particular difficulties for hypoglycemic diabetics. The greater proportion of commercially available test strips is however used by this target group.

A storage container for test elements is described in U.S. patent application U.S. Pat. No. 4,717,018 in which a stopper for closing the orifice is located directly on the container itself with the purpose of preventing the loss of the stopper. Also in this embodiment of the invention a relatively large exertion of force to open and close the cap is required. Furthermore, the removal of the test strip occurs by tipping the container such that the test strips can slip through the orifice. Any given user of this storage container has to make sure that the test strips do not fall out of the container and become soiled when the strips are tipped out which could rule out their intended proper application as a diagnostic test.

A system for containing test elements is described in the laid-open specification DE 43 28 815 in which the opening of the vessel occurs using a slider with which the container lid is slid back. This system is simple and requires little application of force. The storage container however comprises a relatively complex mechanical make-up which incurs expensive production costs. This is the reason why this system is preferably employed as a refill system.

The object of this invention is to make available a storage container for test strips which is simple to use and requires little application of force to effect usage. Moreover it is the object of the present invention to simplify the removal of test strips from the container and to make it easily discernible for users when the storage container is not properly closed. Above all, the novel storage container should be cheap and easy to make.

The objects were accomplished in accordance with this invention by a storage container for test strips comprising a holder which can be closed by a lid connected to the holder by a hinge whereby on the inner side of the cap an elastic seal is located which rests on the rim of the orifice to the holder and is held in the closed position by a releasable locking means. In the closed position of the storage container the seal is compressed and returns to the uncompressed resting position after the locking means is released such that the lid is rotated around the hinge axis and the container is at least partly opened. In accord with the invention it is important that the opening of the storage container occurs automatically after releasing the locking means without any further necessity of action by the user. In the mechanical resting position the storage container is therefore open.

The test strips of the invention have a test zone onto which a sample liquid such as blood or urine can be applied. The sample induces a detectable change such as for example a color change which can be exploited to detect the presence and/or concentration of analyte in the sample. The test strips are usually longitudinally elongated because of the more convenient handling characteristics of this geometry. Many commercially available types of test strip are moisture sensitive and have to be stored closed to ensure the reliability of the analytical determination.

The storage container of the invention has a holder in which the test strips are located. The holder can have a square, rectangular or circular cross-section. It has proven to be advantageous for the purposes of handling when the holder cross-section is oval in form. The holder has an orifice bordered by a rim. It has proven to be of advantage when this rim lies entirely in one plane. Furthermore it is favorable when the orifice does not lie within a lateral surface but rather that an entire end of the holder is open such that the rim surface of the holder orifice is situated perpendicular to the longitudinal axis of the holder. The length of the holder is dictated primarily by the length of the longitudinally extended test strips. In practice, the length of the holder is selected such that it is not significantly larger or smaller than that of the test strips.

Possible materials for the holder are those with a sufficient stiffness. Particularly suitable are plastics such as polyethylene, polypropylene and polystyrene.

The storage container has moreover a lid which is connected to the holder by a hinge. The shape of the lid is selected such that it closes the orifice of the holder like a cap. Construction materials for the lid are those which are used for the holder. It is particularly preferred when the holder and the lid are fabricated from the same type of material as this allows the storage container to be produced as one single component. The hinge which connects the holder and the lid can for example be a joint hinge or a film hinge. A film hinge can be employed to advantage because in this case low cost production in an injection molding process is then possible. A significant feature of the invention at hand is that on the inner side of the lid an elastic seal is positioned and is positioned in such a manner that it creates a seal with the rim of the holder. Appropriate materials for the seal are cellular rubber, styrene elastomers, polyolefine elastomers, polyamide elastomers, polyester elastomers and polyurethane elastomers. Sealing rings fabricated from the designated materials may be glued or welded into the inside of the lid. In a particularly preferred embodiment of the invention, the lid is produced in a hard-/soft injection molding process. In this process the hard lid is initially injected and the soft sealant rubber is injected onto it. Vice versa an injection of the container onto the sealant rubber is also possible. This process has the advantage of greater process reliability because the assembly of the seal is achieved by injection molding and in so doing, separate production steps and also manual manufacturing stages can be avoided. The employment of the overmolding-method further reduces the production costs.

A particularly advantageous embodiment results from this process when polypropylene or polyamide are used as materials for the lid and for the elastic sealant materials such as styrene elastomers or polyolefine elastomers are selected. Suitable elastomers in the sense of the invention have a Shore hardness (DIN 53 505) of 30 to 80, preferably between 55 and 64.

An especially important aspect is the geometrical arrangement of the seal relative to the rim of the holder opening. It has turned out to be of advantage when the cross-section of the seal takes the form of an L and is arranged in such a manner that between the lid and the seal a groove forms whose distance is generated by the shorter segment of the L. In this arrangement the rim of the holder rests in the groove when the storage container is closed and the seal presses from the inside of the holder against the rim of the holder. To ensure the formation of a suitable seal, the width of the groove between the seal and the lid are selected such that it is smaller than the thickness of the material of the holder. Upon closure the holder rim is therefore jammed in the groove whereby the seal is deformed. Because of this deformation the storage container remains in a closed position under a certain mechanical tension which results in an opening of the storage container when the locking means is released. This effect can be reinforced by subjecting the hinge to the tension of a spring. It is furthermore possible in addition to the described seal to employ elastic material in the region of the spring which is compressed when the storage container is closed.

Whereas storage containers described in the prior art are based on the intention of utilizing the resting position of the storage container such that the container is closed, the present invention utilizes the opposite possibility. The storage container remains in a visibly open position when it is not restrained by the locking means. This has the advantage that when the storage container is not closed, it is visibly open. This can prevent the imperfect closing of the container without the user being aware of the fact. The storage container is preferably 20° to 60° open in the resting position.

In addition to the embodiment of the invention already described in which the rim of the holder is situated in a groove, a further possible embodiment of the invention is one in which the seal presses against the rim of the holder. This embodiment is at first sight less complicated but however makes greater demands on the mechanical tolerances of the holder orifice and the seal.

As described already, the mechanical resting position of the storage container of the invention is in the open position. In this position the lid is rotated about 30° relative to the closed position. In the closed position the storage container is held by a locking means. In general the locking moans may be engagement moans on the lid and on the holder which serve to hold the storage container closed, said engagement means may comprise locking means. For this locking means, the embodiments described in the prior art can be considered. It has proven to be particularly advantageous when the lid has a peg or a knob in its inner surface which slots into a depression in the outer surface of the holder when in the closed position. By pressing against a point on the holder in the vicinity of the depression or by pulling at the lid, the lid can be released manually. It is furthermore also possible to release the lid by a deformation of the storage container, or example by pressing it in. In a further embodiment the closing means has a depression or a recess into the lateral surface of the lid into which a peg located on the external surface of the holder can lock. The possibilities for releasing the locking means correspond with those of the embodiments previously described. For both exemplary locking means, it is advantageous when the locking means has a flap or tongue which rests on the surface of the holder when the storage container is closed. The elements of the closing means at the side of the lid can be advantageously in the area of the tongue.

The locking means may be opened in a particularly user-friendly manner by a slide which is located on the storage container. The slide has guide elements which fit into guiding elements on the storage container in such a fashion that a sliding of the slide in the direction of the longitudinal axis of the storage container is possible. Such guide elements can for example have a tongue and groove construction. When the storage container is closed, the slide is located in an initial position in which an edge of the slide is located on the locking means or tongue or is at least in the vicinity of these components.

By sliding the slide in the direction of the lid, the locking device is released. It is particularly advantageous when the edge of the slide tapers and the edge of the locking means which comes into contact with this leading edge of the slide likewise is tapered. In sliding the slide, the edge of the slide slides its way under the locking means or tongue and thereby achieves a release of the locking means. After the sliding of the slide, the side is located in a secondary position from which it can be manually slid back into the initial position. When a tapered edge is used for the slide, the moving of the slide back into the initial position can occur however simply by moving the locking means back towards the closed position.

The use of a tongue on the lid has a further advantageous effect. In the opening of the storage container the locking means is released, the lid then rotated by the user 80° to 150° about the axis of the hinge and the whole device is somewhat tipped so that the test carriers can slide out. In the devices detailed in the prior art (U.S. Pat. No. 4,717,018), the user has to take care that the strips do not unduly fall out of the container. By use of the aforesaid tongue this can be prevented. When the locking means with tongue is opened by rotating about 80° to 90°, preferably 90°, the tongue of the lid is in relation to the opening of the holder in such a proximity as primarily dictated by the breadth of the lid. Advantageously the breadth of the lid is selected such that it is smaller than the length of the test strips but however is large enough to allow convenient manual withdrawal of the test strips in practice this is the case when the breadth of the lid is approximately in the region of 2 to 4 cm. If the storage container has the afore-mentioned tongue located at the locking means, then the test strips slip against the tongue when the storage container is tipped and may easily be manually withdrawn from there. The tongue acts then as a baffle plate. Furthermore it is favorable when the tongue is bent at the edges so that it fits the outer contours of the holder in the closed position. The curvature of the tongue is also favorable for the withdrawal of test strips because the curvature prevents them unduly slipping out via the sides.

The storage container can be sealed advantageously by a label which can be placed over the holder and lid. The labels act then as an originality seal. Such an originality seal can be applied to particular advantage when the lid has a tongue whose outer side forms a flush contour with the holder.

In the field of clinical diagnostics, it is often necessary to label the storage container or the test strips with the number of the production lot from which the test elements stem. In the storage container of the invention an additional chamber may be provided which is accessible from the outside but which is however separated from the inside of the storage container. In this chamber, which preferably has the shape of a slit, a data storage device may be housed on which is stored information concerning the test strips contained in the storage container. In this way it is possible to render the storage container reusable after exhaustion of the contents because when filling with new test strips takes place, only the data storage device has to be replaced. To ensure proper storage of the test elements, normally also a replacement of the desiccant should occur.

Test strips described in the prior art are usually sensitive to moisture. Although the storage container of the invention when closed offers good protection against invading moisture, it is advantageous to furnish the inside of the storage container with a desiccant, because after every opening of the container atmospheric moisture enters the container. By providing the inside of the container with a desiccant, the correct functioning of the test strips can be guaranteed over a longer period. The desiccant can be incorporated in the bottom of the storage container where it can be separated from the test strips by a moisture permeable membrane (such as cardboard). Suitable desiccants have been detailed for quite some time in the prior art. Suitable are for example molecular sieve, silica gel etc.

The present invention also describes a method for providing test strips in which a storage container filled with test strips is opened by releasing the locking means, the lid being rotated about the axis of the hinge and the storage container being so tipped that test strips slide to the lid. The test strips can be withdrawn manually from here. After withdrawal, the storage container is closed by the user by rotation of the lid and closing the locking means.

Furthermore, the subject of the invention is a method for the production of a device in accordance with the invention in which the holder, lid and hinge can be injected as one component and the seal on the inner side of the lid can be adjoined to it by a hard/soft injection molding method (overmolding-process).

The present invention is illustrated in more detail by the following figures:

FIG. 1. Lateral view of the storage container

FIG. 2. Frontal view of the storage container

FIG. 3. Cross-section of the storage container along the line 3—3 in FIG. 2

FIG. 3A. is a more detailed view of the hinge and seal structure, taken at A of FIG. 3.

FIG. 3B is a more detailed view of the engagement of the recess and knob, taken at B of FIG. 3.

FIG. 4. Cross-section through the storage container with two open positions of the lid FIG. 5. Cross-section of a second embodiment of the storage container with the locking means open and closed FIG. 6A is a cross section of another embodiment of the storage case of the invention.

Figure 1:
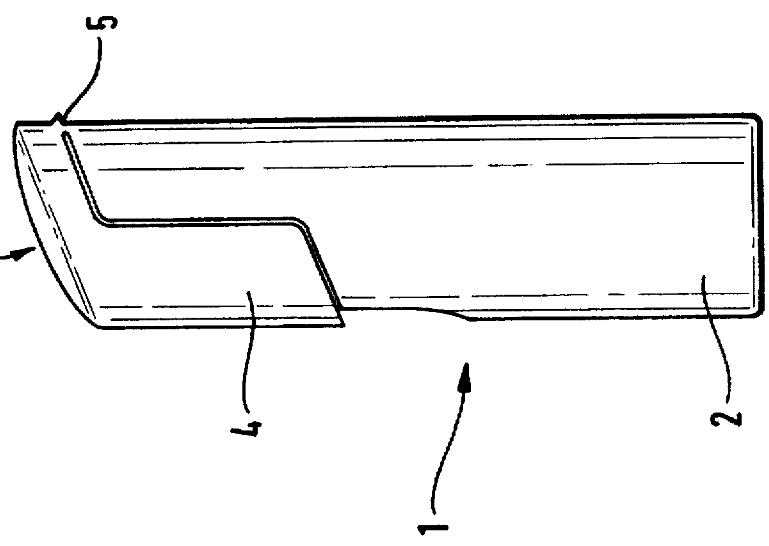

FIG. 1 illustrates the lateral view of the outside of the storage container of the invention for longitudinally extended test strips. The storage container (1) has a holder (2) and a locking means (3) which are connected to each other by a film hinge (5). The locking means (3) has a tongue (4) which when the storage container is closed rests on the outer lateral surface of the holder (2). The Storage container illustrated in FIG. 1 was fabricated from polypropylene as one single component by injection-molding.

Figure 2:
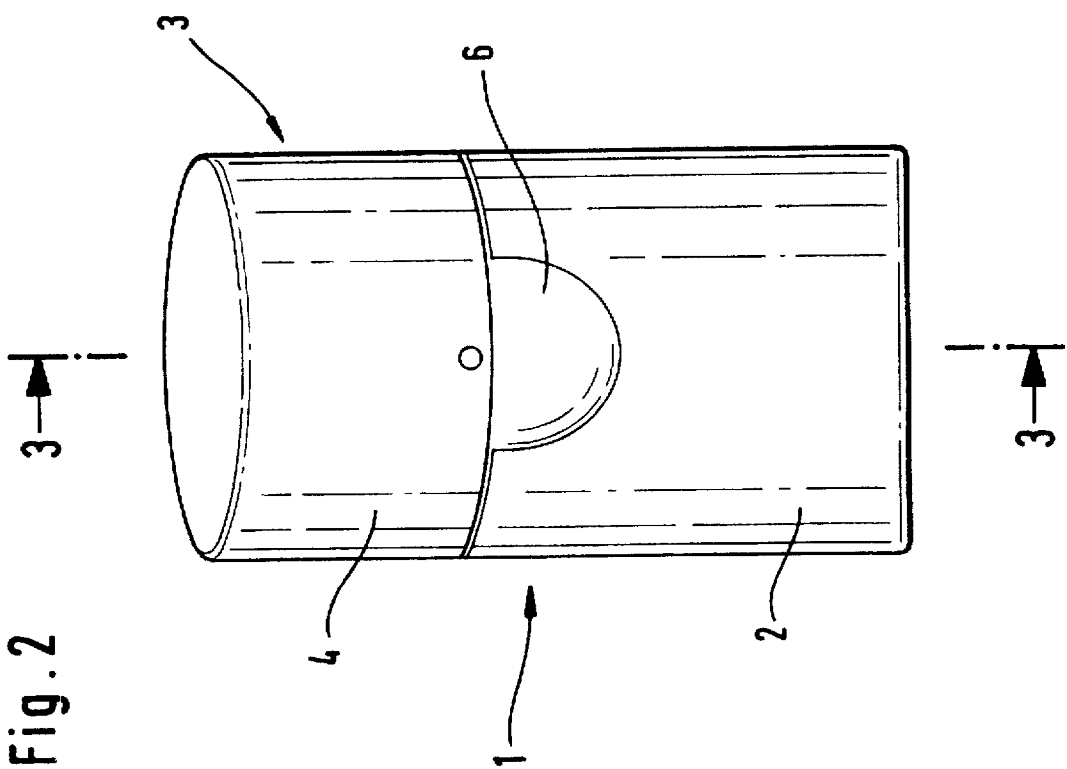

FIG. 2 illustrates a frontal view of the storage container (1). One can recognize that the cross-section of the storage container is oval, which has proven to be favorable for the handling. In FIG. 2 furthermore, a recess (6) in the holder is discernible which has the purpose of providing the user with the possibility of opening the storage container. To open it, the user can either press on the indentation (6) and thereby release the locking means or he can by virtue of the recess press under the edge of the tongue (4) and effect release.

Figure 3:
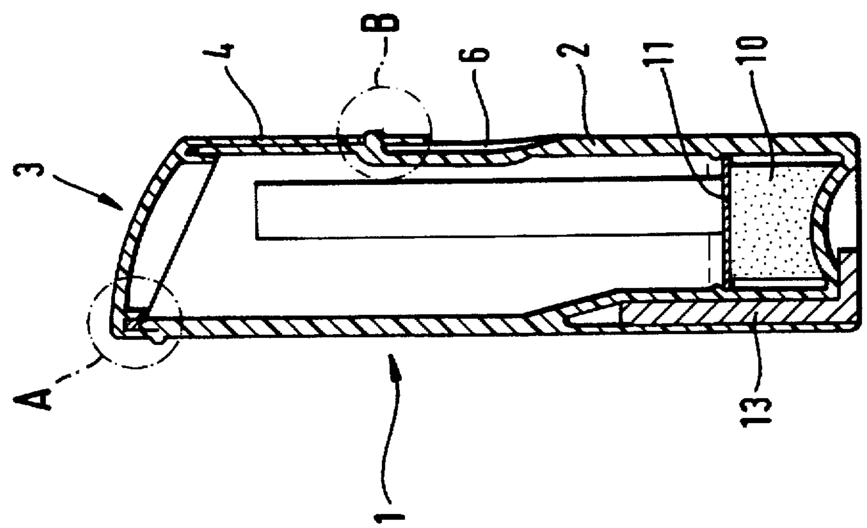
Figure 3B:
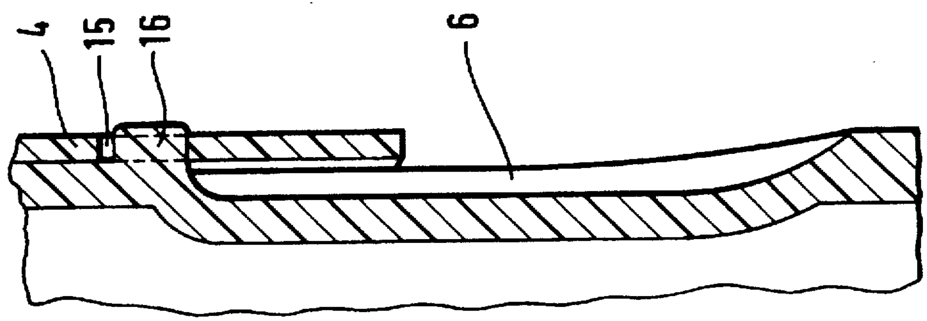
Figure 3A:
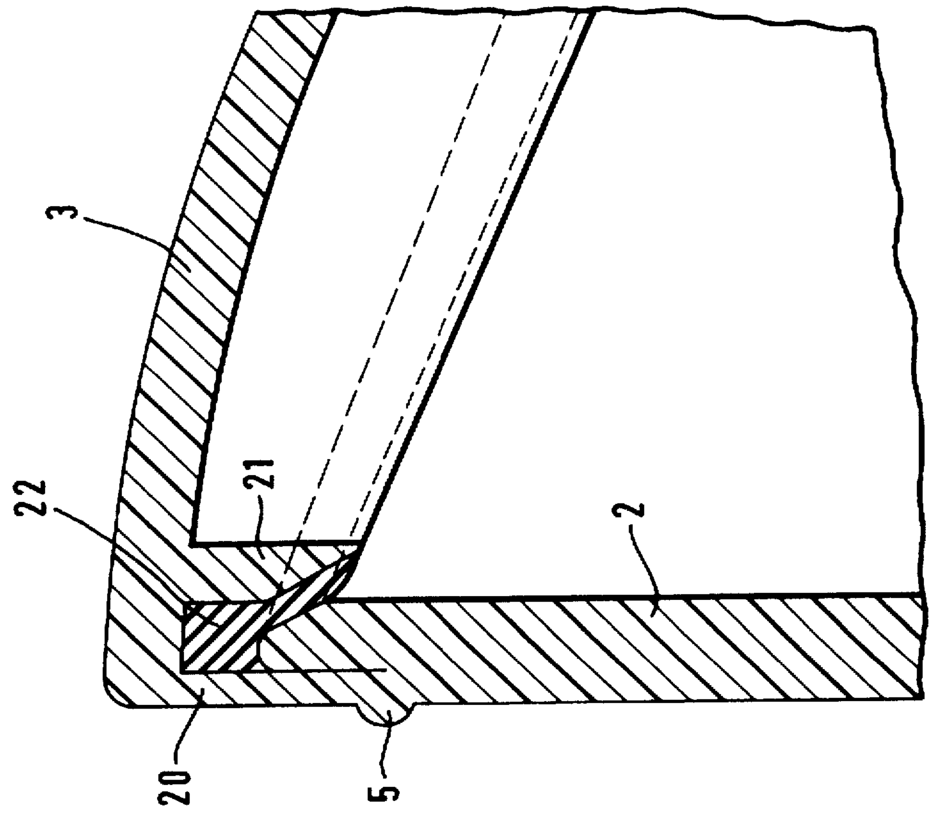

FIG. 3 shows a cross-section of a storage container along the 3—3 line displayed in FIG. 2. FIG. 3 illustrates how the closing means (3) and the rim of the holder orifice dock. This is illustrated in a more detailed manner in the enlarged view displayed in FIG. 3A. The locking means (3) has an outer edge (20), which forms a lateral surface of the closing device. On the inside of the locking means (3) there is a ring-shaped border edge (21). The edges (20) and (21) form a circular groove. A seal made from a styrene elastomer (22) is located in the groove. When the storage container is closed, the rim of the holder compresses the seal (22). The portion of the seal (22) which engages the rim has an L-shaped cross section which is deformed when the lid is closed as shown in FIG. 3A.

A locking means is illustrated in FIG. 3. The section enlargement in FIG. 3B illustrates a further possible embodiment of the locking means. A recess (15) is located in the closure tongue (4) which is docked to a knob (16). The indentation (6) in the holder adjoins the knob (16) in such a manner that pressure exerted on the indentation (6) moves the knob (16) away from the recess (15) and the locking means opens. The mechanical tension in the compressed seal (22) leads to a rotation of the lid (3) about the axis of the film hinge (5) and the lid (3) snaps open.

Furthermore, in FIG. 3 a desiccant chamber (10) is discernible which is located in the floor of the container. The desiccant chamber is separated from the rest of the inside of the storage container by a cardboard cover (11) which is moisture permeable so that test strips do not come into direct contact with the desiccant. Moreover a slit-shaped chamber can be seen in FIG. 3 in the storage container which is accessible from the bottom side of the storage container. A data storage device (13) is housed in this chamber which can be manually removed from the chamber. Information on the test strips, e.g. lot-specific data in the form of a bar code or chip can be loaded on the data storage device.

Figure 4:
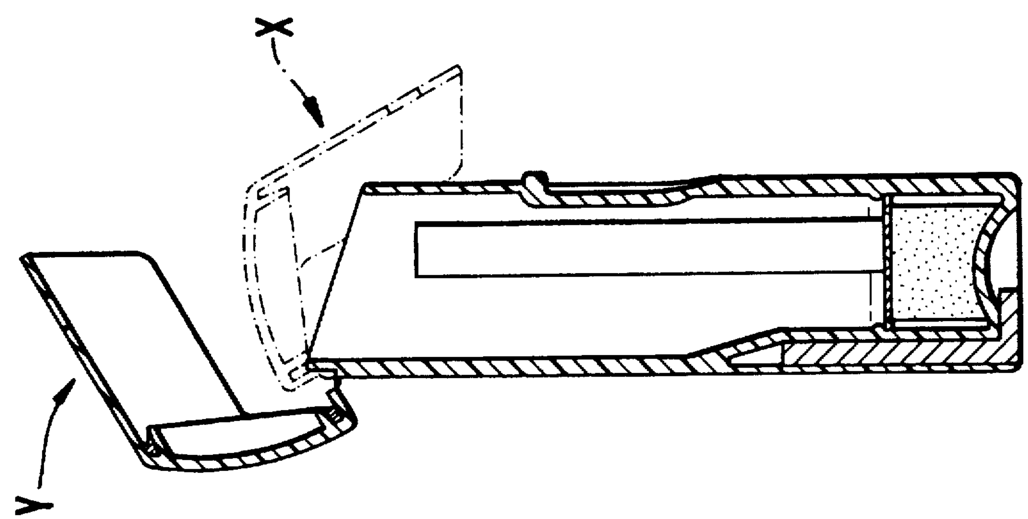

FIG. 4 displays two open positions of the storage container. In the open position X, the lid is open about 30° relative to the fully closed position. When the locking means is released the lid springs open to this position.

The open position Y corresponds with a position in which the lid is brought by the user before removing test strips. In this position the opened lid is at an angle of approximately 110° relative to the closed position.

Figure 5:
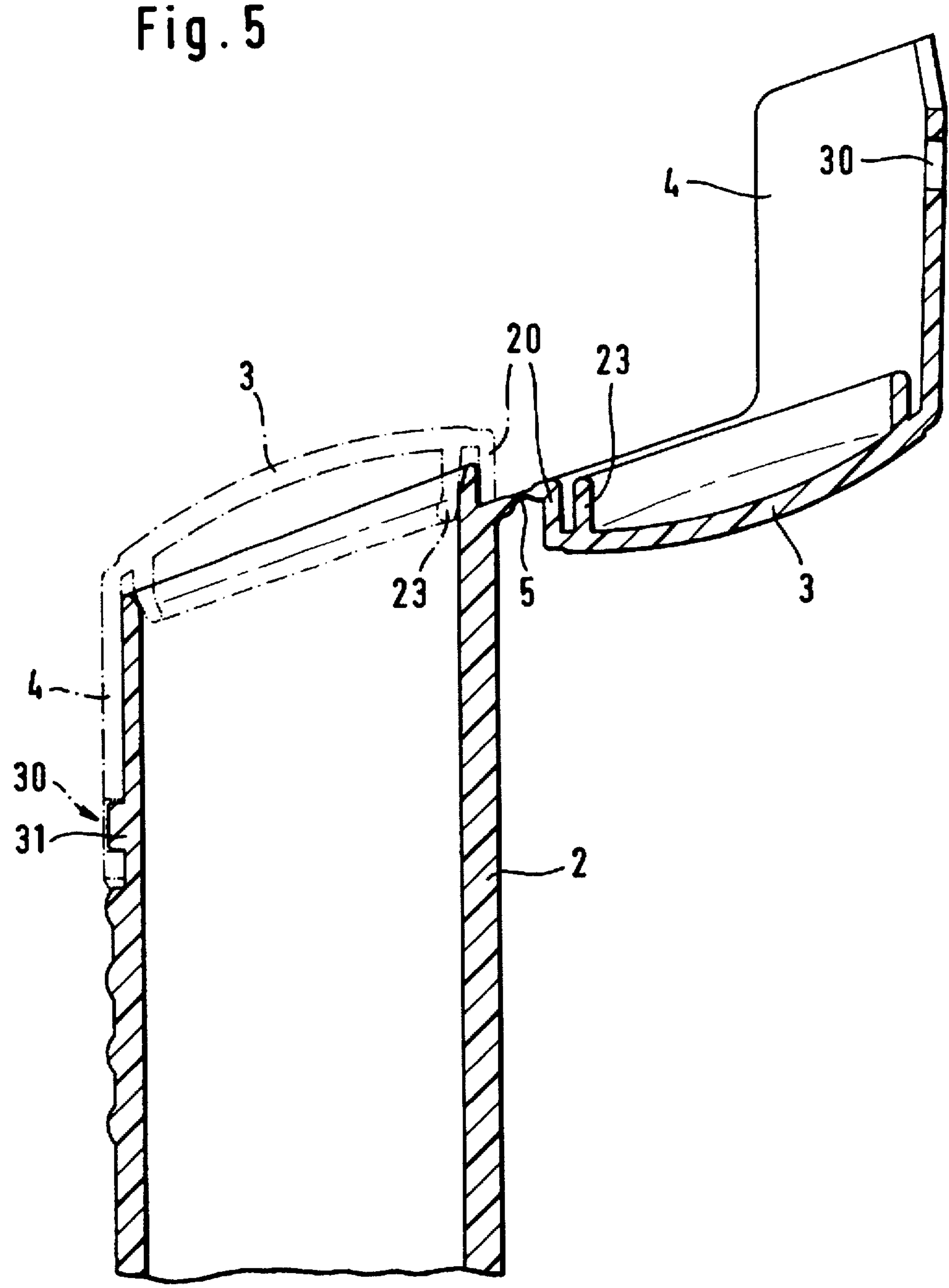

FIG. 5 illustrates a modified embodiment of the storage container of the invention. This embodiment differs from the previously described with respect to the sealing against invading moisture.

The lid is in two parts. The first part corresponds to the first embodiment and possesses an outer edge (20) as well as a tongue (4). The seal in this case is produced by a surrounding annular ring (23) with an L-shaped cross-section. The annular ring (23) is fixed in such a manner that together with the outer edge (20) it forms a surrounding groove. The breadth of this groove is determined by the smaller segment of the L-shaped annular ring. The longer segment of the annular ring (23) forms an inner rim, which is analogous to the inner edge (21) of the embodiment described before. In FIG. 5 the storage container is displayed in an open and in a closed position. The open position corresponds to the state of the storage container when it appears from the injection molding process. When closed, the film hinge (5) is bent but retains the tendency to at least partially return to its initial position because of its original injection-molded form. The spring tension of the film hinge supports the springing open of the storage container after the locking means has been released. FIG. 5 illustrates furthermore how the annular ring (23) is deformed by the rim of the holder orifice in the closed position. The rim of the holder orifice wedges itself between the outer edge (20) and the annular ring (23) thereby pressing the annular ring in. As in the embodiment previously described, the deformation of the elastic annular ring creates a tension which facilitates the opening of the storage container as soon as the locking means is released.

The locking means shown in FIG. 5 consists of a recess (30) in the tongue (4) on the lid and a knob (31) which is located on the outer peripheral surface of the holder (2).

The application of additional elastomers in the hinge region can be explained by recourse to FIG. 5. Elastomers are applied to the right and/or to the left above the hinge (5), which are compressed when the storage container is closed. It has proven to be to advantageous to apply a plurality of knobs or pegs which are in an erect position.

Figure 6B:
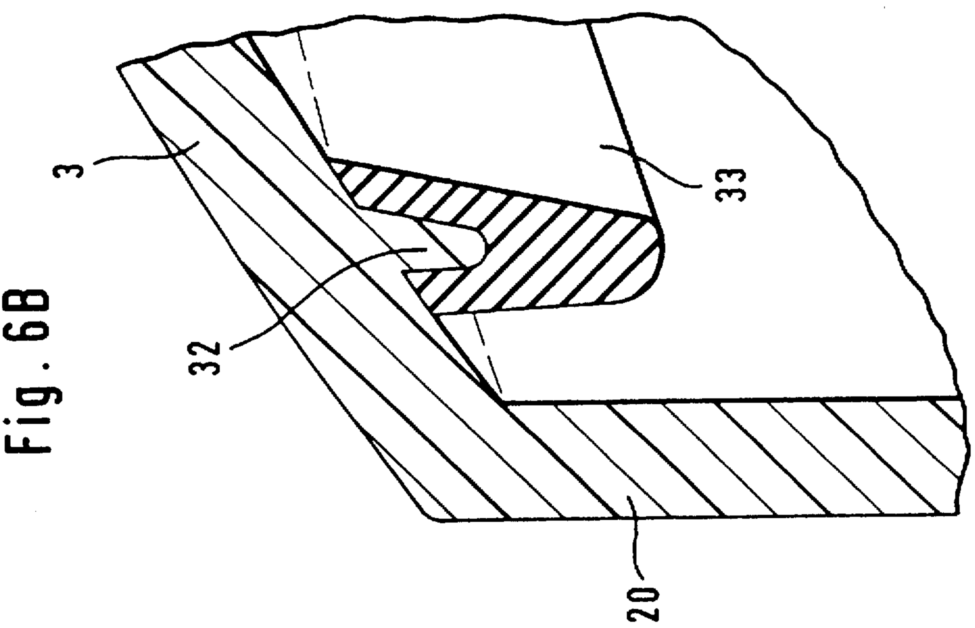
FIG. 6B is a more detailed view of the seal of the embodiment of FIG. 6A.
Figure 6A:
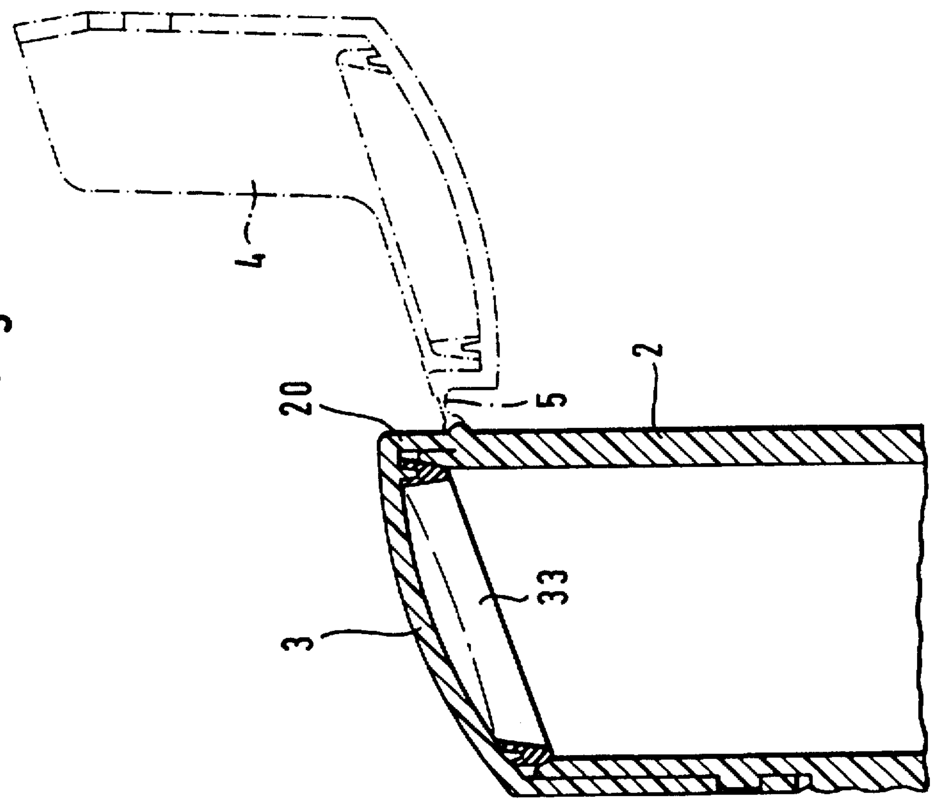

A further embodiment of the storage container is displayed in FIG. 6. In FIG. 6A the upper region of the storage container can be seen. Generally speaking this model corresponds with the one displayed in FIG. 5. FIG. 6A and FIG. 6B however, exhibit a further possibility for the seal. An surrounding ring-shaped edge (32) is located on the inside of the lid (3) which is produced as a single component with the lid. A sealing rim (33) is injected onto the ring-shaped encircling edge whose shape mainly corresponds to that of the inner edge (21) of the lid device (FIG. 3A). In FIG. 6A the storage container is displayed in the open and closed position. In the closed position the sealing rim (33) is deformed by the edge of the holder and therefore is under mechanical tension. After release of the locking means, the storage container springs open due to this mechanical tension.

Figure 7C:
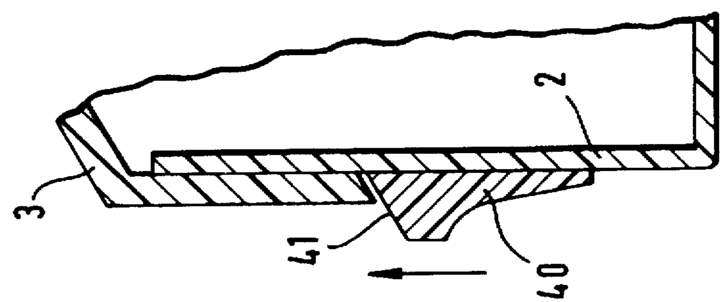
FIG. 7C is a cross section of the slide on the container of the embodiment of FIG. 7A.
Figure 7B:
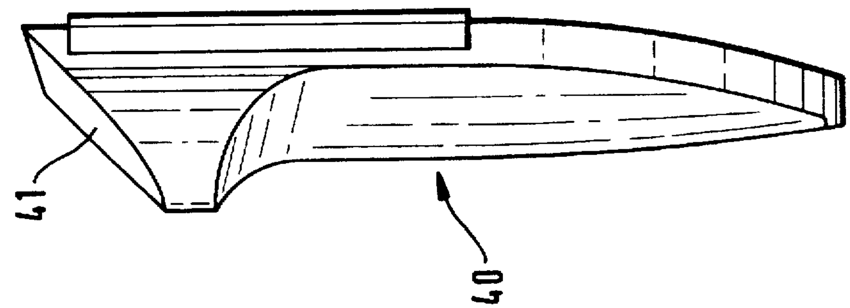
FIG. 7B is a more detailed view of the slide of FIG. 7A
Figure 7A:
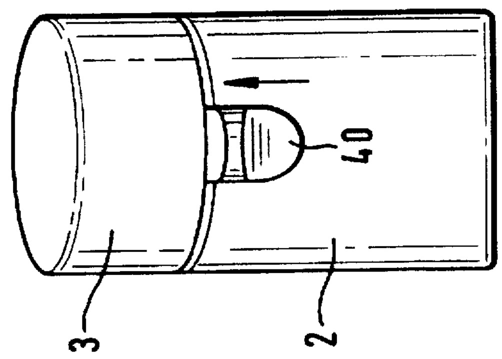
FIG. 7A is a front view of still another embodiment of the storage container which includes a slide for opening the container.

FIG. 7 illustrates a storage container with a slide (40) for the opening of the closing device (3). The opening procedure occurs by movement of the slide in the direction indicated by the arrow.

FIG. 7B details a favorable slide (40) shape with an edge (41) which is tapered. The interaction of the tapered edge with the lid (3) can be seen more clearly in FIG. 7C. The slide is located partially underneath the lid and penetrates by sliding like a wedge between the lid and the holder (2) of the storage container.

List of reference numerals (1) Storage container
(2) Holder
(3) lid
(4) Tongue on the lid
(5) Film hinge
(6) Indentation in the holder
(10) Desiccant chamber
(11) Cover for desiccant chamber
(13) Data storage device
(15) Recess
(16) Peg
(20) Outer edge of the lid
(21) Inner edge of the lid
(22) Seal
(23) Annular ring (elastic)
(30) Recess
(31) Peg/Knob
(32) Ring-shaped surrounding edge
(33) Seal rim
(40) Slide
(41) Tapered edge

We claim:

1. A storage container for test strips, said storage container comprising:

a holder having a cavity therein, with a first side of said cavity forming an orifice defined by a rim;

a lid hingably connected to said holder, said lid including an elastic seal on an inner side thereof, said elastic seal having a shape which corresponds to said rim of said orifice, said elastic seal engaging said rim when said lid is in a closed position closing said orifice; and engagement means on said lid and on said holder for engaging said lid and said holder, thereby holding said lid in the closed position;

wherein said elastic seal is configured to deform against said rim when said lid is moved to the closed position and the engagement means is engaged, and wherein the elastic seal is configured to return to a nondeformed state when the engagement means is released, and wherein the elastic seal returning to the non-deformed state provides a force which moves the lid to a partially open position upon a release of said engagement means.

2. A storage container as recited in claim 1, wherein said engagement means comprises a first engagement element on said holder and a second, corresponding engagement element on said lid.

3. A storage container as recited in claim 1, wherein said hinge is configured to move said lid to the partially open position when the engagement means is released.

4. A storage container as recited in claim 1, wherein the lid comprises a plastic of a first elasticity, and the elastic seal is fabricated from a plastic of a second elasticity, said plastic of said second elasticity being more elastic than the plastic of the first elasticity, said elastic seal being applied to the lid by an injection molding process.

5. A storage container as recited in claim 1, wherein the deformation of said elastic seal is a compression deformation.

6. A storage container as recited in claim 1, wherein said lid comprises an outer annular ridge on an outer periphery thereof, and an inner annular ridge on the inner side of said lid, with a gap between said inner and outer annular ridges, and wherein the elastic seal is located in the gap.

7. A storage container as recited in claim 1, said lid comprising an inner annular ridge on the inner side thereof, wherein said elastic seal surrounds said annular ridge.

8. A storage container as recited in claim 1, wherein said elastic seal has an L-shaped cross section, and is disposed on the inner side of the lid.

9. A storage container as recited in claim 1, wherein said lid comprises one of polypropylene and polyamide, and wherein said elastic seal comprises one of styrene elastomer and polyolefin elastomer.

10. A storage container as recited in claim 1, wherein said holder has a cross-section of an oval shape.

11. A storage container as recited in claim 1, wherein said lid is hingably connected to said holder by a film hinge.

12. A storage container as recited in claim 1, wherein said lid is hingably connected to said holder by a film hinge, and wherein said holder, said hinge, and said lid are formed of a single injection molded component.

13. A storage container as recited in claim 1, wherein said engagement means comprises a recess on a lateral surface of the lid and a projection on an outer surface of the holder, wherein upon an engagement of the lid with the holder, the projection engages the recess to hold the storage container in a closed position.

14. A storage container as recited in claim 1, wherein said engagement means comprises a projection on an inner lateral surface of the lid and a corresponding recess an outer surface of the holder.

15. A storage container as recited in claim 1, wherein said lid includes a tongue portion thereupon, said engagement means engaging said tongue portion.

16. A storage container as recited in claim 1, wherein said lid is hingably connected to said holder whereby said lid can be rotated by up to 190° from the closed condition with respect to the holder.

17. A storage container as recited in claim 16, wherein said lid includes a tongue portion which is configured such that when said lid is at a fully open condition, said tongue intersects a longitudinal axis of said cavity, thereby forming a baffle to restrict contents of the cavity from being removed from the cavity.

18. A storage container as recited in claim 1, wherein said holder includes an outer chamber thereupon, said outer chamber being accessible to receive identification data therein, said outer chamber being configured to enable access to said identification data.

19. A storage container as recited in claim 1, further comprising desiccant means disposed in said cavity.

20. A storage container as recited in claim 1, further comprising desiccant means disposed on the inner side of said lid.

21. A storage container as recited in claim 1, wherein said lid is hingably connected to said holder by a hinge, said hinge providing an opening force sufficient to open said lid by 20° to 60° after release of said engagement means.

22. A storage container as recited in claim 1, wherein said engagement means includes a slide being slidably attached to said holder, said slide having an edge which engages the lid upon slidably movement thereof in a predetermined direction, thereby releasing the engagement means.

23. A storage container as recited in claim 22, wherein said edge is tapered.

24. A storage container as recited in claim 1, wherein said elastic seal comprises an annular ridge disposed on the inner side of the lid, said annular ridge engaging the rim when the lid is closed, thereby sealing the cavity.

25. A storage container as recited in claim 1, wherein a second side of the cavity is closed by a bottom surface of the holder.

26. A storage container as recited in claim 25, further comprising a desiccant means disposed in said cavity adjacent said bottom surface of said holder.

27. A storage container as recited in claim 1, wherein said engagement means comprises locking means for lockingly engaging said lid and said holder.

28. A storage container as recited in claim 8, wherein a surface of said elastic seal which forms said L-shaped cross section engages said rim when said lid is in the closed position.

29. A method for accessing test elements in a storage container, said method comprising the steps of:

providing a storage container including a holder having a cavity therein, with a first side of said cavity forming an orifice defined by a rim, with a lid hingably connected to the holder and including an elastic seal on an inner side thereof, with the elastic seal having a shape which corresponds to the rim of the orifice, with the elastic seal engaging the rim when the lid is in a closed position, and an engagement means for engaging the lid and the holder, thereby holding the lid in the closed position, wherein the elastic seal is configured to deform against the rim when the lid is moved to the closed position, and the engagement means is engaged, and wherein the seal is configured to a return to a non-deformed state when the engagement means is released, and wherein the elastic seal returning to the non-deformed state provides a force to move the lid to a partially open position upon a release of said engagement means;

providing said storage container with test strips and in a closed condition with said engagement means engaged; said method further comprising the steps of opening said engagement means, thereby releasing the lid to enable the elastic seal to move the lid to a partially opened position;

tilting the storage container such that said test strips slide through the orifice through the force of gravity, and wherein said test strips contact said lid in said partially open position.

30. A method for accessing test elements as recited in claim 29, wherein said step of providing the storage container includes providing a bottom surface on a second side of said cavity.

* * * * *